(12) United States Patent
Uemura et al.

(10) Patent No.: US 8,735,596 B2
(45) Date of Patent: May 27, 2014

(54) PROCESS FOR PRODUCING CRYSTALS OF POLYMORPHIC 2-(3-CYANO-4-ISOBUTYL-OXY PHENYL)-4-METHYL-5-THIAZOLE-CABOXYLIC ACID BY POOR-SOLVENT ADDITION METHOD

(75) Inventors: Akihito Uemura, Iwakuni (JP); Tomoaki Nogata, Iwakuni (JP); Takumi Takeyasu, Iwakuni (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 13/382,264

(22) PCT Filed: Jul. 14, 2010

(86) PCT No.: PCT/JP2010/062291
§ 371 (c)(1),
(2), (4) Date: Jan. 4, 2012

(87) PCT Pub. No.: WO2011/007895
PCT Pub. Date: Jan. 20, 2011

(65) Prior Publication Data
US 2012/0108821 A1    May 3, 2012

(30) Foreign Application Priority Data
Jul. 15, 2009   (JP) ................................. 2009-166755

(51) Int. Cl.
*C07D 277/34* (2006.01)
(52) U.S. Cl.
USPC ........................................................ 548/201
(58) Field of Classification Search
None
See application file for complete search history.

(56) References Cited

U.S. PATENT DOCUMENTS 6,225,474 B1    5/2001  Matsumoto et al.
2010/0317702 A1*  12/2010  Piran et al. .................... 514/365

FOREIGN PATENT DOCUMENTS

| CN | 1275126 A | 11/2000 |
|---|---|---|
| CN | 101139325 A | 3/2008 |
| CN | 101684107 A | 3/2010 |
| CN | 101684108 A | 3/2010 |
| EP | 1020454 | 7/2000 |
| JP | 2003-261548 | 9/2003 |
| WO | WO 99/65885 A1 | 12/1999 |
| WO | 2010144685 | 12/2010 |

OTHER PUBLICATIONS

Pavia et al., Introduction to Organic laboratory Technique a Microscale Approach. Orlando: Saunders College Publishing, 1990.*
Kitamura, M. et. al., "Crystallization and transformation behavior of the polymorphs of thiazolederivative", Abstract of Autumn Meeting of the Society of Chemical Engineers, Japan, vol. 33, p. 653, Aug. 12, 2000.
Communication for EP 10 79 9952 dated Nov. 6, 2012, with Supplementary European Search Report dated Oct. 30, 2012.
Kitamura et al., "Effects of solvent composition and temperature on polymorphism and crystallization behavior of thiazole-derivative", Journal of Crystal Growth, 236:676-686 (2002).
Kitamura et al., "Effective of Temperature on Antisolvent Crystallization and Transformation Behaviors of Thiazole-Derivative Polymorphs", Crystal Growth & Design, 6(5):1214-1218 (2006).
Office Action issued on Jun. 11, 2013 from Israeli Patent Office in a counterpart Israeli Application No. 217509.
"Polymorphism in Pharmaceutical solids", edited by H.G. Brittain, Marcel Dekker, D.J.W. Grant; (Chapter 1); p. 1-10 and J.K. Guillory (Chapter 5); p. 183-226, 1999.
L.M. Harwood et al., "Experimental Organic Chemistry, Principles and Practice", Blackwell Science Ltd., p. 127-136, 1989.
Office Action issued on Dec. 9, 2013 from the Intellectual Property Office of Singapore in Singapore Application No. 201200305-9.

* cited by examiner

*Primary Examiner* — Michael Barker
*Assistant Examiner* — Po-Chih Chen
(74) *Attorney, Agent, or Firm* — Sughrue Mion, PLLC

(57) ABSTRACT

Disclosed is a process for producing A-form crystals of 2-(3-cyano-4-isobutyloxyphenyl)-4-methyl-5-thiazolecarboxylic acid, comprising: a step of dissolving by heating 2-(3-cyano-4-isobutyloxyphenyl)-4-methyl-5-thiazolecarboxylic acid in one or a plurality of solvents as a good solvent, selected from the group consisting of 1-propanol, 2-propanol, ethanol, and acetone; a step of cooling the solution; and a step of adding to the solution a hydrocarbon solvent as a poor solvent.

1 Claim, 1 Drawing Sheet

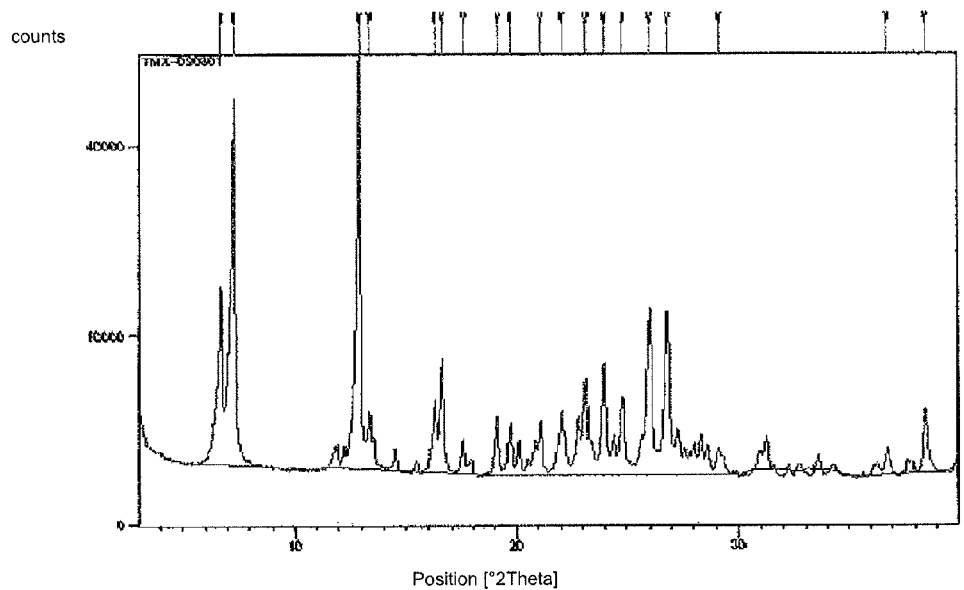
Peak list
| Pos.[°2Th.] | Net intensity [cts] | FWHM [°2Th.] | d-spacing [Å] | Relative intensity [%] |
|---|---|---|---|---|
| 6.7172 | 14698.42 | 0.0669 | 13.15922 | 24.33 |
| 7.3031 | 49028.04 | 0.0836 | 12.10474 | 81.15 |
| 12.9335 | 60413.65 | 0.0836 | 6.84505 | 100.00 |
| 13.3926 | 2699.66 | 0.0836 | 6.61145 | 4.47 |
| 16.2766 | 3580.13 | 0.1171 | 5.44589 | 5.93 |
| 16.6186 | 6872.47 | 0.1004 | 5.33459 | 11.38 |
| 17.5918 | 1368.28 | 0.1338 | 5.04160 | 2.26 |
| 19.1391 | 2575.99 | 0.1338 | 4.63737 | 4.26 |
| 19.7047 | 2245.86 | 0.0836 | 4.50552 | 3.72 |
| 21.1033 | 2308.52 | 0.1171 | 4.20997 | 3.82 |
| 22.0856 | 2385.00 | 0.2676 | 4.02489 | 3.95 |
| 23.1375 | 5119.95 | 0.1004 | 3.84423 | 8.47 |
| 23.9359 | 6454.61 | 0.1338 | 3.71778 | 10.68 |
| 24.8151 | 3939.06 | 0.1338 | 3.58802 | 6.52 |
| 25.9976 | 12382.36 | 0.1506 | 3.42744 | 20.50 |
| 26.8063 | 12034.96 | 0.1673 | 3.32585 | 19.92 |
| 29.1541 | 770.01 | 0.3346 | 3.06314 | 1.27 |
| 36.7951 | 893.27 | 0.2676 | 2.44270 | 1.48 |
| 38.4654 | 3024.85 | 0.1171 | 2.34039 | 5.01 |

PROCESS FOR PRODUCING CRYSTALS OF POLYMORPHIC 2-(3-CYANO-4-ISOBUTYL-OXYPHENYL)-4-METHYL-5-THIAZOLE-CABOXYLIC ACID BY POOR-SOLVENT ADDITION METHOD

CROSS REFERENCE TO RELATED APPLICATIONS

This application is a National Stage of International Application No. PCT/JP2010/062291 filed Jul. 14, 2010, claiming priority based on Japanese Patent Application No. 2009-166755, filed Jul. 15, 2009, the contents of all of which are incorporated herein by reference in their entirety.

TECHNICAL FIELD

The present invention relates to a process for producing A-form crystals of 2-(3-cyano-4-isobutyloxyphenyl)-4-methyl-5-thiazolecarboxylic acid. The compound has an activity of regulating biosynthesis of uric acid in vivo and can be used, for example, as a therapeutic agent for hyperuricemia.

BACKGROUND ART

In producing drugs, control of crystal polymorphs of chemical substances, the bulk powder, is recognized as an important matter because a difference in the polymorphs has a great influence on the properties as a drug such as a pharmaceutical function, bioavailability, stability, and the like. This is as stated in the ICH (International Conference on Harmonisation) Q6A guideline, "Specifications: Test Procedure and Acceptance Criteria for New Drug Substances and New Drug Products: Chemical Substances."

With regard to the polymorphs of 2-(3-cyano-4-isobutyloxyphenyl)-4-methyl-5-thiazolecarboxylic acid, PTL 1 discloses presence of 5 kinds of polymorphs, including A-form crystals, B-form crystals, C-form crystals, D-form crystals, and G-form crystals, as well as an amorphous material. Also disclosed are methods for producing the same. The methods for producing the polymorphs disclosed herein are for producing each of the polymorphs, comprising: adding a predetermined amount of a mixed solvent of methanol or 2-propanol and water to 2-(3-cyano-4-isobutyloxyphenyl)-4-methyl-5-thiazolecarboxylic acid; dissolving the mixture by stirring under heat; setting the methanol/water composition and the like and temperature to predetermined values by addition of water and cooling; and thereafter collecting crystals by filtration and drying the same.

However, influences of the initial concentration referred to in PTL 1 are only on the chemical purity and the amounts of the recovered product, and effects on the polymorphs obtained are not described. In addition, in the case of crystallization from a mixed solvent of 2-propanol and water, it is only described that the G-form crystals are obtained.

Furthermore, at International Symposium on Industrial Crystallization (Sep. 21-25, 1998, Tianjin, China), M. Kitamura, M. Hanada, K. Nakamura, and others have shown in "Crystallization and transformation behavior of the polymorphs of thiazole-derivative" (see NPL 1) that, under the condition of a methanol/water composition and temperature where only the A-form crystals were thought to be obtained, the G-form crystals or a mixture of the A-form crystals and the G-form crystals were obtained in some cases at the time of crystallization, when water addition time was drastically changed substantially. In addition, they have also shown that, by subsequently changing the temperature of the crystallization liquid and by keeping the liquid in a state of agitation, the crystals were transformed to the D-form crystals.

When industrially useful A-form crystals are to be produced, these heretofore known methods are not pronounced to be completely free from contamination by the G-form crystals. Moreover, in order to avoid contamination by the G-form crystals, the water addition time is restricted and, thus, there is also a problem that a long time is required for industrial production.

Meanwhile, PTL 2 discloses a method for producing the polymorphs by addition of water to 2-(3-cyano-4-isobutyloxyphenyl)-4-methyl-5-thiazolecarboxylic acid dissolved in methanol or a mixed solvent of methanol/water, wherein the initial concentrations and water addition time are varied to obtain the A-form crystals, the G-form crystals, or a mixture of A-form and the G-form crystals of 2-(3-cyano-4-isobutyloxyphenyl)-4-methyl-5-thiazolecarboxylic acid.

However, crystallization using these heretofore known mixed solvent systems, for example crystallization using a mixed solvent system of methanol/water with a ratio of 7/3 provides crystals of a form different from the A-form crystals or a mixture of A-form crystals and crystals of a form different therefrom. Thus, it has not been possible to obtain the A-form crystals stably.

CITATION LIST

Patent Literature

PTL 1: International Publication No. WO99/65885
PTL 2: Japanese Patent Laid-Open Publication No. 2003-261548

Non Patent Literature

NPL 1: M. Kitamura and K. Nakamura, "Crystallization and transformation behavior of the polymorphs of thiazole-derivative," Abstract of Autumn Meeting of the Society of Chemical Engineers, Japan, Vol. 33, p. 653 (2000 Aug. 12)

SUMMARY OF INVENTION

Technical Problem

An object of the present invention is to selectively and stably obtain the A-form crystals of 2-(3-cyano-4-isobutyloxyphenyl)-4-methyl-5-thiazolecarboxylic acid under conditions suitable for commercial production.

Solution to Problem

The present invention is a process for producing A-form crystals of 2-(3-cyano-4-isobutyloxyphenyl)-4-methyl-5-thiazolecarboxylic acid, comprising: a step of dissolving by heating 2-(3-cyano-4-isobutyloxyphenyl)-4-methyl-5-thiazolecarboxylic acid in one or a plurality of solvents as a good solvent, selected from the group consisting of 1-propanol, 2-propanol, ethanol, and acetone; a step of cooling the solution; and a step of adding to the solution a hydrocarbon solvent as a poor solvent.

That is, the present invention is based on the finding that the A-form crystals can be obtained stably by using a lower alcohol solvent except methanol or acetone as the good solvent and by using a hydrocarbon solvent as the poor solvent.

Here, the A-form crystals of 2-(3-cyano-4-isobutyloxyphenyl)-4-methyl-5-thiazolecarboxylic acid refer to a polymorph which shows an X-ray powder diffraction pattern having characteristic peaks at, when represented in terms of a reflection angle 2θ, about 6.62°, 7.18°, 12.80°, 13.26°, 16.48°, 19.58°, 21.92°, 22.68°, 25.84°, 26.70°, 29.16°, and 36.70°. One example of such X-ray powder diffraction patterns is shown in FIG. 1 (the X-ray diffractometer used is different from the one used in PTL 1). Alternatively, in an infrared spectroscopic analysis, the A-form crystals may be expressed as a polymorph having a characteristic absorption at around 1678 $cm^{-1}$, which is distinguishable from other polymorphs (see PTL 1).

Advantageous Effects of Invention

In contrast to crystallization using water as the poor solvent, the conventional technology, where crystals are obtained under certain conditions as solvates, hydrates, or a mixture thereof; the production process of the present invention has an effect that the A-form crystals can be obtained selectively and stably by using a hydrocarbon solvent as the poor solvent.

That is, according to the production process of the present invention, the A-form crystals of 2-(3-cyano-4-isobutyloxyphenyl)-4-methyl-5-thiazolecarboxylic acid can be produced under conditions suitable for commercial production, while lowering the possibility of intermingling of other crystal forms.

BRIEF DESCRIPTION OF DRAWINGS

FIG. 1 shows an X-ray powder diffraction pattern and a peak list of the A-form crystals of 2-(3-cyano-4-isobutyloxyphenyl)-4-methyl-5-thiazolecarboxylic acid.

DESCRIPTION OF EMBODIMENTS

The present invention is a process for producing the A-form crystals of 2-(3-cyano-4-isobutyloxyphenyl)-4-methyl-5-thiazolecarboxylic acid, comprising: a step of dissolving by heating 2-(3-cyano-4-isobutyloxyphenyl)-4-methyl-5-thiazolecarboxylic acid in one or a plurality of solvents as a good solvent, selected from a group consisting of 1-propanol, 2-propanol, ethanol, and acetone; a step of cooling the solution; and a step of adding to the solution a hydrocarbon solvent as a poor solvent.

When a plurality of solvents are used as the good solvent, they may be mixed in advance and used as a mixed solvent or each solvent may be added successively.

Here, the ratio of solute/solvent when dissolving the solute in a good solvent is as follows: when the solvent is ethanol, 1-propanol, or 2-propanol, the ratio is preferably in a range from 0.05 to 0.5 g/mL and, further, more preferably in a range from 0.08 to 0.25 g/mL; and when the solvent is acetone, the ratio is preferably in a range from 0.05 to 0.1 g/mL and, further, more preferably in a range from 0.08 to 0.09 g/mL.

Conditions for a cooling operation in the production process of the present invention are not particularly limited as long as an effect as crystallization is manifested.

As such conditions, there may be considered temperature before and after cooling, a period of time for cooling (further, a time curve of the liquid temperature), means for cooling such as cooling devices and the like, presence or absence of stirring, stirrers and rate of stirring when stirring is used, vessels to be used, and the like.

Regarding these, one skilled in the art may find suitable conditions for given prerequisites by referring to Examples, mentioned later while considering necessary amounts of crystals, period of time, costs, available equipment, and the like.

If necessary, the conditions may be determined by preliminary experiments. In addition, the temperature before cooling must be determined by considering the boiling point of the solvent used. Further, if the temperature after cooling is too low, there may be formed solvates depending on the solvent used and, therefore, it is desirable to confirm the conditions beforehand. Further, when acetone is used as the good solvent, care must be taken because other crystal forms may get intermingled if the solution is not cooled rapidly. From this viewpoint, also, it is desirable that the conditions are confirmed in advance.

One example of the period of time for cooling is ca. 15 minutes (except when the solvent is acetone).

As a hydrocarbon solvent used as the poor solvent, preferable are heptane and/or hexane and, especially preferable is heptane.

Furthermore, the amount of such poor solvent is such that the ratio of solute/(poor solvent added) is preferably in a range from 0.05 to 0.4 g/mL and, further, more preferably in a range from 0.06 to 0.4 g/mL.

In the production process of the present invention, the order of the step of cooling a solution of 2-(3-cyano-4-isobutyloxyphenyl)-4-methyl-5-thiazolecarboxylic acid and the step of adding a poor solvent to the solution is not particularly limited. Either step may be carried out first, or whole or part of these steps may be carried out concurrently.

In the conventional production process where water is used as a solvent, there is a possibility that the crystals may be transformed to solvates depending on the method of drying after crystallization and the like. However, in the production method of the present invention, water is not used as the solvent and, therefore, there is no possibility of transformation of the crystals to the hydrates, enabling use of a variety of methods as the drying method after crystallization.

In the production process of the present invention where a hydrocarbon solvent is used as the poor solvent, the hydrocarbon solvent does not form solvates with 2-(3-cyano-4-isobutyloxyphenyl)-4-methyl-5-thiazolecarboxylic acid, thus providing a wide stable region in crystallization conditions for obtaining the desired A-form crystals. Further, in the production process of the present invention, when 1-propanol or 2-propanol is used as the good solvent, no solvates with 2-(3-cyano-4-isobutyloxyphenyl)-4-methyl-5-thiazolecarboxylic acid are formed, thus providing a wide stable region in crystallization conditions for obtaining the desired A-form crystals. Based on these findings, when a combination of 1-propanol or 2-propanol and a hydrocarbon solvent, especially heptane, is used as the solvent, the A-form crystals can be obtained stably over wider solvent ratios and a wider range of temperature than the conventional art.

In addition, because the solvents used in the present production process are only organic solvents without using water, the present process has superiority also in that it provides higher purification efficiency for hydrophobic impurities.

EXAMPLES

Example 1

To 10 g of 2-(3-cyano-4-isobutyloxyphenyl)-4-methyl-5-thiazolecarboxylic acid was added 57 mL of ethanol and the mixture was heated to complete dissolution. While maintaining the solution at 40° C. or higher, 133 mL of heptane was added thereto. This solution was cooled to 40° C. and crystals which separated were collected by filtration, followed by drying. The crystals obtained were analyzed by X-ray powder diffraction and were found to be A-form crystals.

Example 2

To 10 g of 2-(3-cyano-4-isobutyloxyphenyl)-4-methyl-5-thiazolecarboxylic acid was added 115 mL of 2-propanol and the mixture was heated to complete dissolution. While maintaining the solution at room temperature or higher, 67 mL of heptane was added thereto. This solution was cooled to room temperature and crystals which separated were collected by filtration, followed by drying. The crystals obtained were analyzed by X-ray powder diffraction and were found to be A-form crystals.

Example 3

To 10 g of 2-(3-cyano-4-isobutyloxyphenyl)-4-methyl-5-thiazolecarboxylic acid was added 40 mL of 1-propanol and the mixture was heated to complete dissolution. While maintaining the solution at room temperature or higher, 80 mL of heptane was added thereto. This solution was cooled to 0° C. and crystals which separated were collected by filtration, followed by drying. The crystals obtained were analyzed by X-ray powder diffraction and were found to be A-form crystals.

Example 4

To 10 g of 2-(3-cyano-4-isobutyloxyphenyl)-4-methyl-5-thiazolecarboxylic acid was added 115 mL of acetone and the mixture was heated to complete dissolution. The solution was cooled rapidly to 15° C. using an ice bath and 67 mL of heptane was added thereto. Crystals which separated were collected by filtration, followed by drying. The crystals obtained were analyzed by X-ray powder diffraction and were found to be A-form crystals.

INDUSTRIAL APPLICABILITY

The A-form crystals of 2-(3-cyano-4-isobutyloxyphenyl)-4-methyl-5-thiazolecarboxylic acid obtained by the production process of the present invention can be used as a drug.

The invention claimed is:

1. A process for producing A-form crystals of 2-(3-cyano-4-isobutyloxyphenyl)-4-methyl-5-thiazolecarboxylic acid, comprising: dissolving by heating 2-(3-cyano-4-isobutyloxyphenyl)-4-methyl-5-thiazolecarboxylic acid in 1-propanol or 2-propanol cooling the resulting solution; and adding to the resulting solution heptane.

* * * * *

UNITED STATES PATENT AND TRADEMARK OFFICE
CERTIFICATE OF CORRECTION

PATENT NO. : 8,735,596 B2  
APPLICATION NO. : 13/382264  
DATED : May 27, 2014  
INVENTOR(S) : Akihito Uemura, Tomoaki Nogata and Takumi Takeyasu Page 1 of 1

It is certified that error appears in the above-identified patent and that said Letters Patent is hereby corrected as shown below:

In the Claims

Column 6, line 24, please insert a --;-- before "cooling the resulting solution".

That is, claim 1 should read as follows:

1. A process for producing A-form crystals of 2-(3-cyano-4-isobutyloxyphenyl)-4-methyl-5-thiazolecarboxylic acid, comprising: dissolving by heating 2-(3-cyano-4-isobutyloxyphenyl)-4-methyl-5-thiazolecarboxylic acid in 1-propanol or 2-propanol; cooling the resulting solution; and adding to the resulting solution heptane.

Signed and Sealed this  
Fourteenth Day of October, 2014

Michelle K. Lee  
*Deputy Director of the United States Patent and Trademark Office*